(12) United States Patent  (10) Patent No.: US 8,888,741 B2
Brunner et al.  (45) Date of Patent: Nov. 18, 2014

(54) BALLOON CATHETER AND METHOD FOR MANUFACTURING SAME

(75) Inventors: Arthur Brunner, Jonen (CH); Adrian Blaser, Zürich (CH); Matthias Wesselmann, Glattfelden (CH); Patrice Bachmann, Winterthur (CH)

(73) Assignee: Biotronik Vi Patent AG, Baar (CH)

( * ) Notice: Subject to any disclaimer, the term of this patent is extended or adjusted under 35 U.S.C. 154(b) by 653 days.

(21) Appl. No.: 12/533,528

(22) Filed: Jul. 31, 2009

(65) Prior Publication Data

US 2010/0030144 A1  Feb. 4, 2010

(30) Foreign Application Priority Data

Aug. 1, 2008 (DE) .......................... 10 2008 040 914

(51) Int. Cl.
 *A61M 25/10* (2013.01)
(52) U.S. Cl.
 CPC ....... *A61M 25/1006* (2013.01); *A61M 25/1034* (2013.01); *A61M 25/1038* (2013.01); *A61M 2025/1004* (2013.01); *A61M 25/1029* (2013.01)
 USPC ...................... 604/103.08; 604/103
(58) Field of Classification Search
 USPC ........ 604/96.01, 103, 103.06–103.09, 103.14
 See application file for complete search history.

(56) References Cited

U.S. PATENT DOCUMENTS

| | | | |
|---|---|---|---|
| 4,994,072 A | 2/1991 | Bhate et al. | |
| 5,334,146 A * | 8/1994 | Ozasa | 604/103.06 |
| 5,522,882 A | 6/1996 | Gaterud et al. | |
| 5,525,388 A | 6/1996 | Wand et al. | |
| 5,826,588 A | 10/1998 | Forman | |

(Continued)

FOREIGN PATENT DOCUMENTS

| | | |
|---|---|---|
| DE | 28 47 633 | 5/1979 |
| DE | 44 80 681 | 4/1996 |

(Continued)

OTHER PUBLICATIONS

European Patent Office, European Search Report corresponding to EP 09164877.4; issued Nov. 30, 2009.

(Continued)

*Primary Examiner* — Nicholas Lucchesi
*Assistant Examiner* — Benjamin Koo
(74) *Attorney, Agent, or Firm* — Greer, Burns & Crain, Ltd.

(57) ABSTRACT

A balloon catheter comprises an outer shaft having a distal end, an inner shaft situated therein to form an annular fluid line and projecting beyond the distal end of the outer shaft, and a balloon which is dilatable under the influence of a fluid introduced through the fluid line under pressure. At its proximal end the balloon is attached in a fluid-tight manner to the distal end region of the outer shaft at a first attachment zone, and at its distal end is attached in a fluid-tight manner to the distal end region of the inner shaft at a second attachment zone. Between the attachment zones, in the undilated state the balloon is placed in longitudinal folds along its length. The balloon, at least at its distal end, has an untapered design with a thin wall thickness (d) which is essentially unchanged over the length of the balloon, and the longitudinal folds extend into the attachment zone at that location.

25 Claims, 10 Drawing Sheets

(56) References Cited

U.S. PATENT DOCUMENTS

| | | |
|---|---|---|
| 6,176,698 B1 | 1/2001 | Grantz et al. |
| 6,287,506 B1 | 9/2001 | Hudgins et al. |
| 7,217,278 B2 | 5/2007 | Tomaschko et al. |
| 2003/0032921 A1* | 2/2003 | Duchamp .................. 604/103 |
| 2003/0105508 A1* | 6/2003 | Johnson et al. ............ 623/1.11 |
| 2003/0180488 A1 | 9/2003 | Lim et al. |
| 2005/0228428 A1 | 10/2005 | Ali et al. |

FOREIGN PATENT DOCUMENTS

| | | |
|---|---|---|
| DE | 696 32 855 | 7/2005 |
| EP | 0 485 903 | 5/1992 |
| WO | WO 95/22367 | 8/1995 |

OTHER PUBLICATIONS

German Patent Office, Search Report for Priority German Application No. 10 2008 040 914.6, Issued Nov. 17, 2008.

* cited by examiner

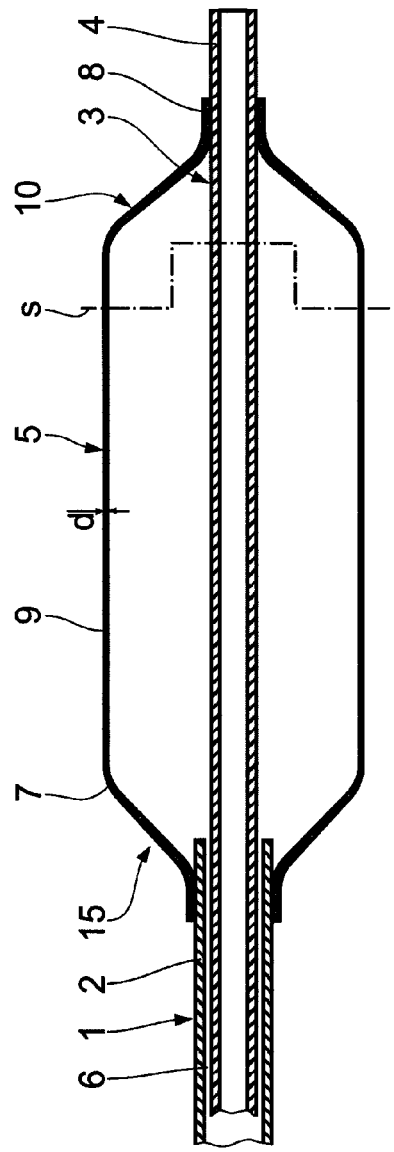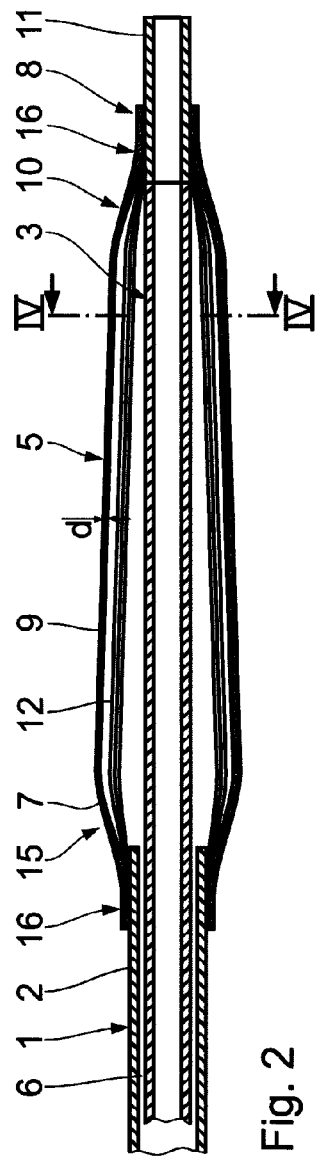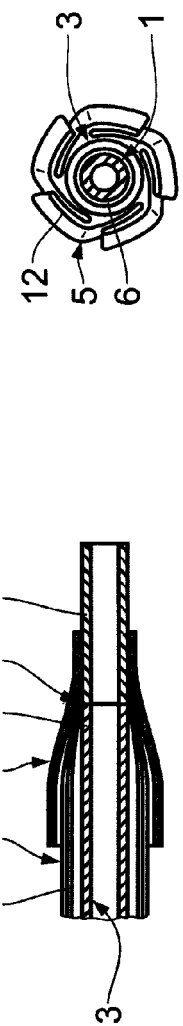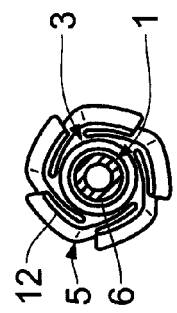

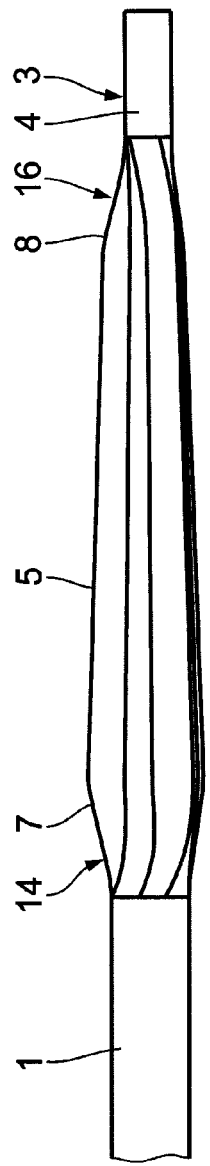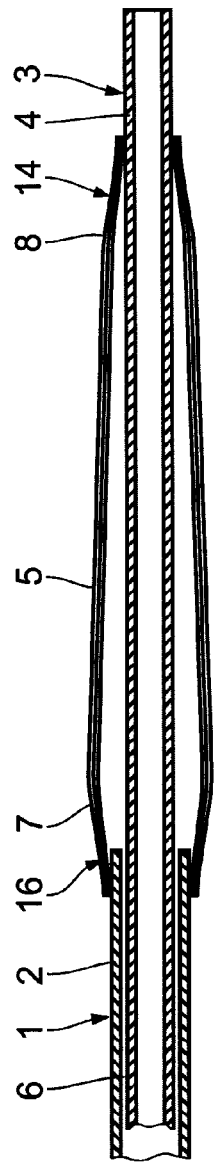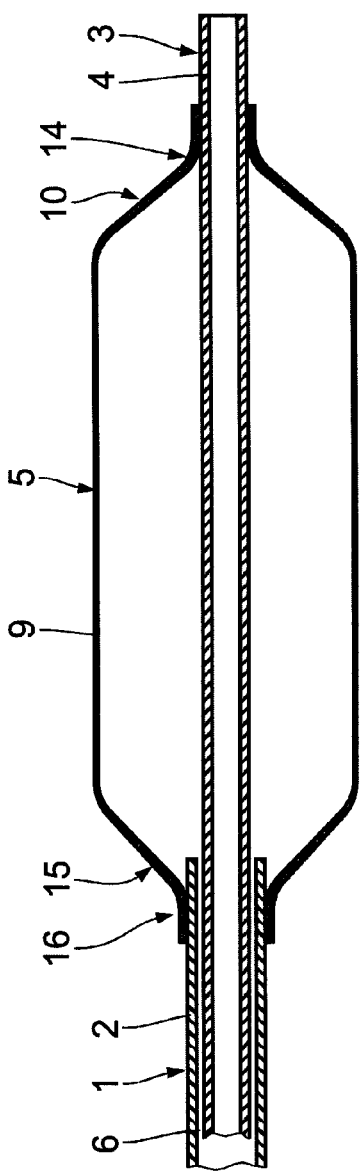

BALLOON CATHETER AND METHOD FOR MANUFACTURING SAME

FIELD OF THE INVENTION

The invention relates to a balloon catheter and a method for manufacturing same.

BACKGROUND OF THE INVENTION

The basic design of balloon catheters as known from documents U.S. Pat. No. 5,522,882 A and U.S. Pat. No. 7,217,278 B2, for example, is stated in the preamble of claim 1. Balloon catheters as used, for example, for expanding abnormally constricted blood vessels in the body or for placing vessel wall supports (referred to as "stents") have an outer shaft with a distal end and an inner shaft, situated therein to form an annular fluid line, projecting beyond the distal end of the outer shaft. At the distal end of the catheter a balloon is attached at its proximal end in a fluid-tight manner to the distal end region of the outer shaft at a first attachment zone, and at its distal end is attached in a fluid-tight manner to the distal end region of the inner shaft at a second attachment zone. Between these attachment zones, in the undilated state the balloon is placed in longitudinal folds in order to minimize its outer diameter in this state. This is necessary to allow the balloon catheter together with the balloon to be pushed at the distal end through narrow vessels or sharply curved vessel regions. After the balloon is set in position at the application site, a fluid under pressure may be introduced through the annular fluid line formed between the inner and outer shafts, and the balloon may be dilated. This causes the longitudinal folds to unfold in the peripheral direction, with a large increase in the diameter of the balloon.

Because of their manufacturing method and design, the balloons of conventional balloon catheters have disadvantages which will become apparent from the following summary of the production process. Balloons are generally manufactured from a plastically distendable plastic tube having an outer diameter of 2.1 mm, for example, and a lumen diameter of 1.5 mm, for example. The wall thickness of this tube is thus 0.3 mm. The ends of the tube are clamped into a holding device, whereupon the lumen is acted on by a fluid pressure.

Between the clamping points the workpiece is inflated and the wall material is drastically stretched, resulting in an essentially cylindrical balloon having a wall thickness of 0.03 mm, for example. From the clamped ends of the balloon preform the wall thickness decreases by a factor of 10, for example, over the tapers at the two ends of the balloon toward the shell wall.

In a further processing step the ends are sized and brought to an outer diameter of 1.8 mm and a lumen diameter of 1.6 mm, for example. The wall thickness is then 0.1 mm, and therefore is still greater than three times the wall thickness in the cylindrical portion of the balloon preform.

When balloons manufactured in this manner are then attached at their ends to the outer and inner shafts of the catheter and longitudinally folded for the undilated state, the ends and tapers of the balloon having a much greater wall thickness are built up much more than the very thin-walled cylindrical shell of the balloon. The folded balloon profile is therefore greatest around the attachment zones at the tapers which form the balloon shoulders. Correspondingly, the balloon also has the greatest stiffness at that location. These greatly built-up end regions of the balloon thus prevent insertion of the catheter into narrow blood vessels. The stiffness of the balloon tapers placed into folds also makes it more difficult to guide the balloon catheter around narrow curvatures or branches of vessels. Lastly, during manufacture of the balloon catheter itself it is difficult to fold the tapered regions having a greater wall thickness.

U.S. Pat. No. 5,522,882 A mentioned above discloses a stent positioning system which includes a catheter in which the dilatable balloon has ends which extend in a stepwise manner. The aim is to avoid the presence of tapered sections of the balloon in the axial direction before and after the stent which is positioned on the catheter. This is achieved by use of sleeve-like attachments which directly adjoin the stent on the end regions of the balloon, so that when the balloon is dilated the tapers are essentially provided as radial annular steps. The problems of the differing wall thicknesses and of folding for conventional balloons are not addressed in this document.

U.S. Pat. No. 7,217,278 B2 teaches a complex finishing of balloon preforms, in that after inflation, wall material is mechanically removed in the region of the tapers and thick-walled ends in order to reduce the wall thickness. In this regard particular care must be taken that this processing step is carried out below the glass transition temperature of the thermoplastic plastic material. Thus, on the whole the manufacture of balloons such as those known from U.S. Pat. No. 7,217,278 B2 is complicated from a production standpoint.

SUMMARY OF THE INVENTION

The object of the present invention is to provide a balloon catheter and a method for manufacturing same, in which by use of a simple design the thickened and stiffened areas present in the prior art as the result of the longitudinally folded tapers are avoided at least at the distal, i.e., the outermost, end of the balloon.

From a production standpoint this object is achieved by the features of claim 1. The principle of the approach provides that the balloon has an untapered design, at least at one end, and therefore has a consistently thin wall thickness over a considerable length. In the undilated state the balloon is folded over its entire length into longitudinal folds which extend into the attachment zone, at least at the distal end of the balloon catheter. At that location the balloon is attached to the distal end region of the inner shaft in a fluid-tight manner with respect to the longitudinal folds, so that no thickening or stiffening results at the distal end of the catheter as the result of the tapering.

The balloon advantageously has an untapered design at its two ends, as discussed above, and at the distal end of the outer shaft is also correspondingly attached to the outer shaft in a fluid-tight manner with respect to the longitudinal folds.

It is seen that despite the folding, over its entire length such a balloon has no thickening in diameter or stiffening as the result of great wall thicknesses. Such a balloon catheter may thus be easily guided at its distal end provided on the balloon through very narrow blood vessels and sharp bends in a vascular system.

According to one preferred embodiment, the untapered balloon is attached at its longitudinal folds to the attachment zones using a shrinkable sleeve with thermoplastic deformation, so that the balloon is welded at its longitudinal folds to the outer or inner shaft of the catheter in a fluid-tight manner.

Further preferred embodiments of the invention relate to a constricting ring which constricts the respective balloon end in front of its attachment zone and thus protects the weld or adhesive bond in the attachment zone from peeling stress. In this manner failure of the balloon during pressure impingement for dilation is reliably prevented.

Further stabilization of the balloon at its ends may be achieved by a counterpressure chamber, provided at the end of the balloon on the other side of the constriction, which maintains the balloon in equilibrium in the region of its fixation and constriction.

The distal end of the balloon, optionally with the constricting ring, may be provided at a pointed taper located at the distal end of the inner shaft, thereby greatly simplifying insertion into the bodily vessel.

A further improvement in the leak-tightness and pressure-tightness of the dilatable balloon is achieved by an inwardly inverted attachment of the balloon ends at the outer or inner shaft. Such an "inwardly rolled configuration" is self-sealing during dilation of the balloon. The weld or glue seam is then subjected only to compression stress when the balloon dilates.

Lastly, an alternative constriction of the dilatable balloon may be provided by twisting in the region in front of the attachment zones of the balloon. Here as well, the connection of the balloon to the respective shaft is protected from peeling stress.

From a process engineering standpoint, the above-referenced object is achieved using manufacturing methods as stated in greater detail in method claims 14 through 16. To avoid unnecessary repetition, the corresponding production processes together with features and advantages result from the following description of exemplary embodiments, to which reference is expressly made herein.

DESCRIPTION OF THE DRAWINGS

These exemplary embodiments are explained in greater detail with reference to the accompanying drawings, which show the following:

FIG. 1 through 3 show schematic longitudinal sections of the distal end region of a balloon catheter in various production steps;

FIG. 4 shows a radial section of the balloon catheter according to section line IV-IV from FIG. 2;

FIG. 8 shows a partial side view of a balloon catheter at its distal end, together with a balloon in the undilated state which is untapered at both ends;

FIGS. 9 and 10 show partial longitudinal axis sections of the balloon catheter at its distal end, in the undilated and dilated states of the balloon, respectively;

DETAILED DESCRIPTION OF THE INVENTION

Figure 5:
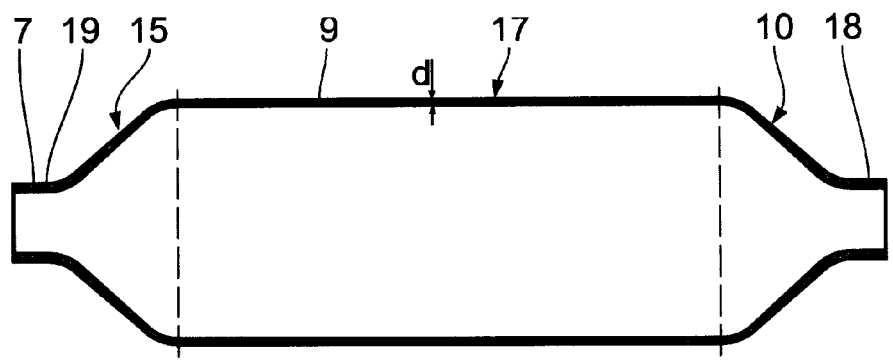
FIG. 5 shows a schematic longitudinal view of a balloon preform.

The manufacture and design of a balloon catheter in a first embodiment are explained in greater detail with reference to FIGS. 1 through 4. The description is based on an essentially two-part catheter shaft, formed from a tubular outer shaft 1 having a distal end 2, and an inner shaft 3 whose outer diameter is much smaller than the inner diameter of the outer shaft and whose distal end 4 projects beyond the distal end 2 of the outer shaft 1 at least by the length of the balloon 5. An annular fluid line 6 is provided between the outer shaft and inner shaft 1, 3, through which an appropriate fluid may be conducted into the balloon 5 under pressure.

FIG. 1 shows the distal end of the balloon catheter in an intermediate production step in which a plastically formable tube having the same length as the balloon 5 has been attached at its proximal end 7 to the distal end 2 of the outer shaft 1, and at its distal end 8 has been attached to the distal end 4 of the inner shaft 3, in both cases in a pressure-tight manner. Introduction of a fluid causes this tube to be brought into the configuration shown in FIG. 1, with the balloon 5 inflated between the respective proximal and distal ends 7, 8. The shell wall 9 of the balloon 5 is thus provided with a very thin wall thickness d which increases, for example by a factor of 10, in the direction toward the respective proximal or distal end 7, 8 over the taper 10, 15 thus formed. The balloon catheter is thus provided with a relatively thick beaded rim, in particular at the distal end 8. The balloon manufactured in this manner is folded tightly in longitudinal folds 12 around the inner shaft 3, starting from the taper 15 and proceeding toward the proximal end 7, as shown particularly clearly in FIG. 4.

In order to remove the beaded rim mentioned above, the balloon 5 and the inner shaft 3 are cut off at the section line s indicated in FIG. 1. Thus, the taper 10 of the balloon 5 facing its distal end 8 is also removed. The balloon 5 is therefore untapered at that location.

As shown in FIG. 2, by use of an extension piece 11 having the same diameter and wall thickness and made of the same or different material as the inner shaft, at its distal end the inner shaft 3 is essentially returned to its original length.

A short shrinkable sleeve section 13 is placed around the balloon 5, which is tightly wrapped around the inner shaft 3 and the extension piece 11. This shrinkable sleeve section is acted on radially and externally by annular heated sealing jaws (not illustrated in further detail), thereby radially shrinking the shrinkable sleeve section 13 and pressing the distal end of the folded balloon 5 against the inner shaft 3 and the extension piece 11 and welding same to these components under the effect of heat. The shrinkable sleeve section 13 is then removed.

In summary, the balloon 5 as manufactured according to FIG. 1 through 4 is secured at its proximal end 7 in an attachment zone 14 on the outer shaft 1, and has a taper 15 as a transition to the shell wall 9. From that point on, the balloon 5 has a thin wall thickness d which is unchanged over its length, and the longitudinal folds 12 extend in an untapered manner toward the distal end 8 of the balloon 5 and into the attachment zone 16 at that location.

The design and manufacture of a balloon catheter in one alternative embodiment having an untapered design at its two ends 7, 8 is explained with reference to FIG. 5 through 10.

The description is based on a balloon preform 17, produced in the customary manner, having thick-walled end sections 18, 19 and tapers 10, 15. Although not indicated in FIG. 5, the illustrated balloon preform 17 may also be produced with an overall length corresponding to a multiple of the length of a balloon 5. After the balloon preform 17 has been folded, for further processing multiple untapered balloons 5 may then be produced from such a balloon preform by cutting to length.

Figure 6:
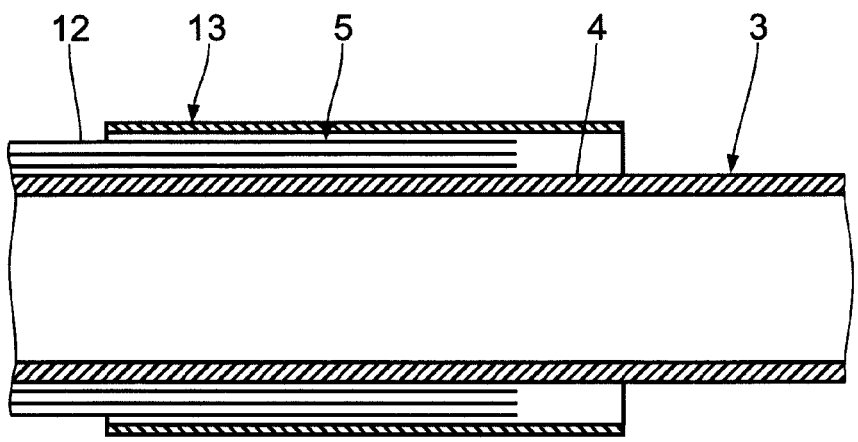
FIGS. 6 and 7 show partial longitudinal axis sections of a balloon catheter in one alternative embodiment, in two successive intermediate production steps in the region of the distal end of the balloon.
Figure 7:
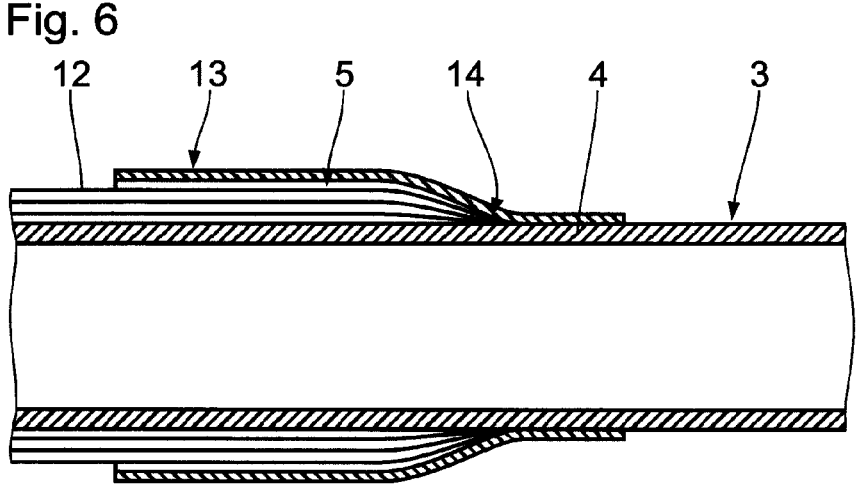

As shown in FIG. 6, to manufacture a balloon catheter having a balloon 5 that is untapered at both ends, the balloon 5 which is cut from the balloon preform 17 is once again folded in longitudinal folds 12 around the respective distal end 2, 4 of the outer shaft and inner shaft 1, 3. In FIG. 6 only the distal end 4 of the inner shaft 3 is shown; the configuration at the outer shaft 1 corresponds to the mirror image of this FIG. As indicated in FIG. 5 by dashed lines, the tapers 10, 15 together with their end sections 18, 19 are then cut off, so that only the thin shell wall 9 of the balloon preform 17 remains. A shrinkable sleeve section 13 is placed around the distal end 8 of the balloon 5, and in the same manner is placed around the proximal end of the balloon (not illustrated), and once again is radially acted on by heating jaws. The balloon 5 is thus thermoplastically welded at its two ends 7, 8 to the inner shaft 3 and outer shaft 1 in a fluid-tight manner, as illustrated in FIG. 7. After the thermoplastic weld connection between the balloon 5 and the outer shaft 1 and inner shaft 3 produced in this manner cools, the shrinkable sleeve section 13 is removed, so that at its distal end the balloon catheter assumes the shape shown in FIGS. 8 and 9. The continuously thin-walled shell wall 9 of the balloon 5 is thermoplastically welded to the distal end 2 of the outer shaft 1 and to the distal end 4 of the inner shaft 3 in the two attachment zones 14, 16 in a fluid-tight manner, with inclusion of the longitudinal folds 12. The balloon 5 thus maintains an optimal low outer diameter at these critical locations, and shows no stiffening.

When this balloon 5 is dilated by introducing a fluid under pressure into the fluid line 6, the balloon is inflated, as indicated in FIG. 10. As the result of unfolding of the longitudinal folds 12, tapers 10, 15 are formed on the balloon 5, but their walls are just as thin as the shell wall 9 of the balloon 5.

Figure 11:
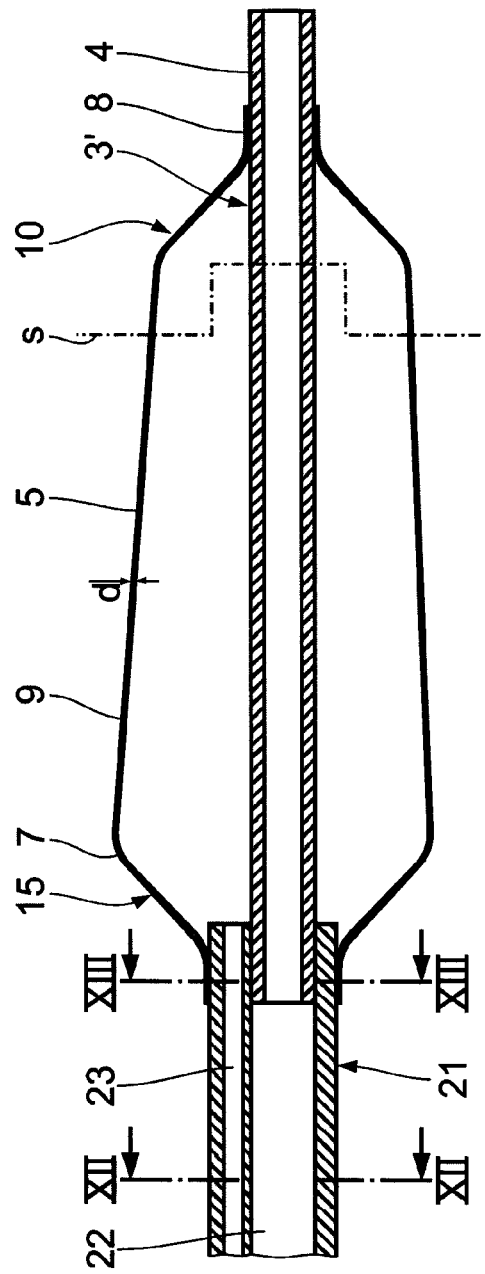
FIG. 11 shows a partial longitudinal axis section of a balloon catheter in a further alternative embodiment.
Figure 13:
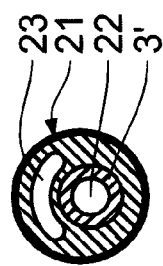
FIGS. 12 and 13 show radial sections of the balloon catheter according to respective section lines XII-XII and XIII-XIII from FIG. 11.
Figure 12:

FIG. 11 through 13 illustrate a further alternative embodiment. In this embodiment the catheter has a dual-lumen shaft 21 comprising a circular, somewhat eccentrically positioned wire lumen 22 and a balloon lumen 23 having an approximately banana-shaped cross section. A guide wire for the balloon catheter may be pushed through the wire lumen 22, and the fluid for dilating the balloon 5 may be conducted through the balloon lumen 23. The wire lumen may be designed as a short lumen extending over only a portion of the length of the catheter for a so-called "monorail variant," or may be designed as a continuous lumen for a so-called "over-the-wire variant." As shown in FIG. 11, as an outer shaft the dual-lumen shaft 21 has no inner shaft in the sense of the exemplary embodiments according to FIG. 1 through 10; instead, an inner shaft 3' is implemented by mounting a short section on the wire lumen 22 of the dual-lumen shaft 21. Analogously to the exemplary embodiment according to FIG. 1 through 4 having a balloon 5, the balloon 5 is then welded to the distal end 2 of the dual-lumen shaft 21 and is welded at the distal end 4 of the short section of the inner shaft 3,' folded, cut off at the distal end 8 together with the taper 10, and finished with an extension piece (not illustrated in FIG. 11) to achieve the balloon configuration at the distal end thereof as illustrated in FIG. 2 through 4.

Figure 14:
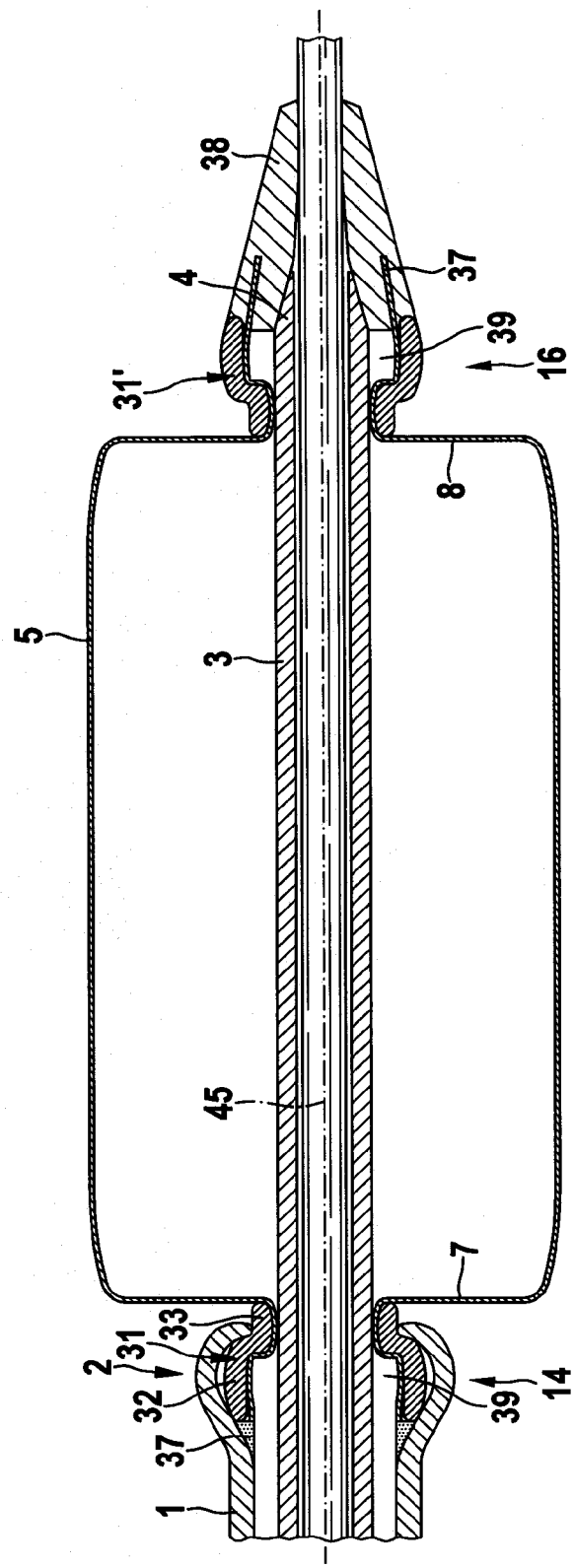
FIGS. 14 through 16 show schematic longitudinal sections of the distal end region of a balloon catheter in embodiments having constricting rings.
Figure 17:
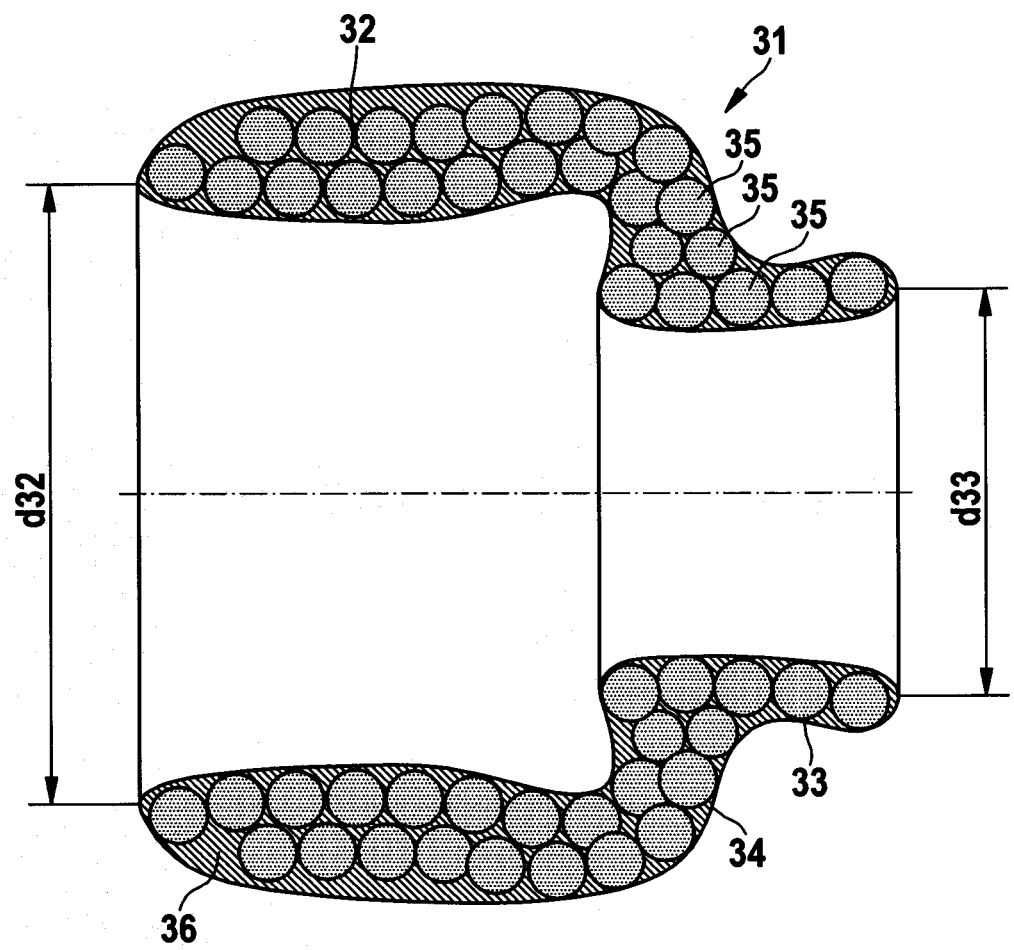
FIG. 17 shows a schematic axial section of a constricting ring.

In the embodiment of the balloon catheter shown in FIG. 14, a constricting ring 31 is inserted at the distal end 2 of the outer shaft 1 which, as shown particularly clearly in FIG. 17, has a longitudinal section 32 with a wide diameter d32 and a longitudinal section 33 with a much smaller diameter d33. The two longitudinal sections 32, 33 are connected via a stepped shoulder 34. In this embodiment the constricting ring 31 is made of a fiber tow 35 situated in a fixation matrix 36 composed of a suitable polymeric binder. The constricting ring may also be a simple ring made of a high-strength material which is then positioned in a tube, for example the outer shaft.

As shown in FIG. 14, the proximal end 7 of the balloon is guided inwardly over the narrow longitudinal section 33 of the constricting ring 31, and is attached at the other side of the wide longitudinal section 32 in the attachment zone 14 thereof with a connection 37 to the inner side of the outer shaft 1. The connection 37 may be a weld or an adhesive bond.

At the distal end 8 the balloon 5 is similarly guided through a constricting ring 31' whose narrow longitudinal section 33 faces the dilatable balloon volume. The end of the balloon is subsequently secured between a pointed taper situated on the distal end 4 of the inner shaft 3.

The passages in the balloon ends 7, 8 situated in the region of the wide longitudinal section 32 are likewise dilated during dilation of the balloon, thus forming counterpressure chambers 39 which provide stabilization of the balloon 5 in the guide formed by the respective constricting ring 31, 31', thus assisting in a reliable, pressure-tight attachment of the balloon 5.

Figure 15:
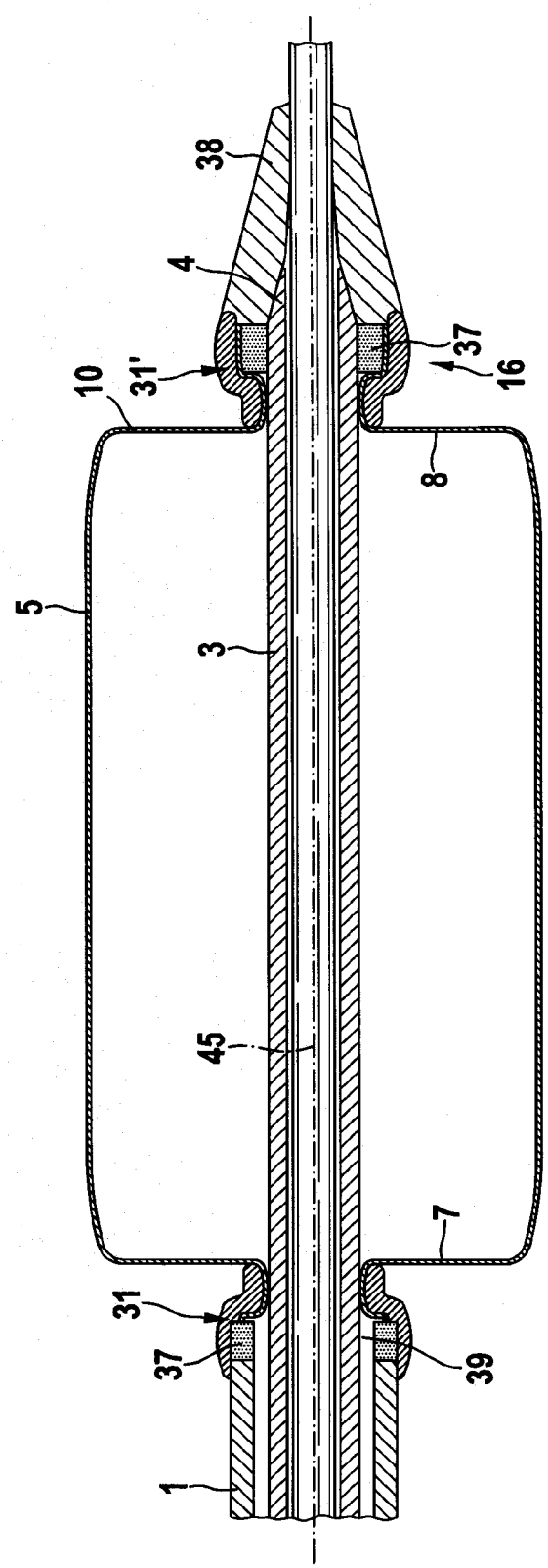

Whereas in the embodiment according to FIG. 14 the constricting ring 31 is pressed with its wide longitudinal section 32 into the slightly expanded outer shaft 1 and is attached at that location, in the embodiment according to FIG. 15 the proximal constricting ring 31 is placed on the outer shaft 1, and the proximal end 7 of the balloon 5 makes a flush connection with the outer shaft 1 via the welded or glued connection 37. The proximal end 7 of the balloon 5 is once again guided through the constricting ring 31, thereby protecting the connection 37 from peeling stress. A counterpressure chamber 39 is provided on the side of the wide longitudinal section 32 of the constricting ring 31.

The distal end 8 of the balloon 5 is likewise guided through a constricting ring 31', which at its wide longitudinal section 32 is attached to the distal end 4 of the inner shaft 3 in front of the pointed taper 38 via a connection 37. The distal end 8 of the balloon 5 is embedded in the connection 37.

Figure 16:
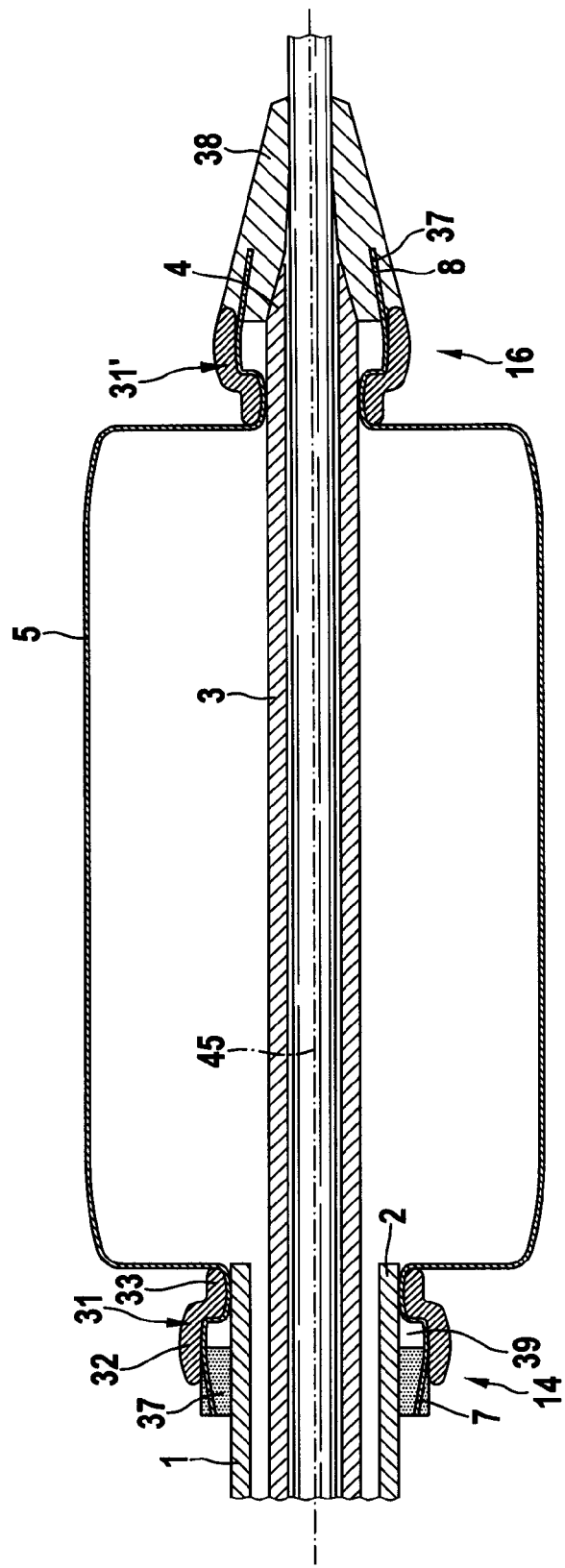

In the embodiment according to FIG. 16, a proximal constricting ring 31 is externally placed on the distal end 2 of the outer shaft 1 and attached via a connection 37. At the same time, the proximal end 7 of the balloon guided through the constricting ring 31 is fixed in place in this connection. In the region of the wide longitudinal section 32 a counterpressure chamber 39 is once again provided between the connection 37 and the constricting ring 31. Overall, the proximal end of the balloon 5 is protected from peeling stress in its attachment zone 14 by means of the constricting ring 31.

The anchoring of the distal end 8 of the balloon 5 corresponds to the embodiment according to FIG. 14, so that repetition of the discussion is unnecessary.

Figure 18:
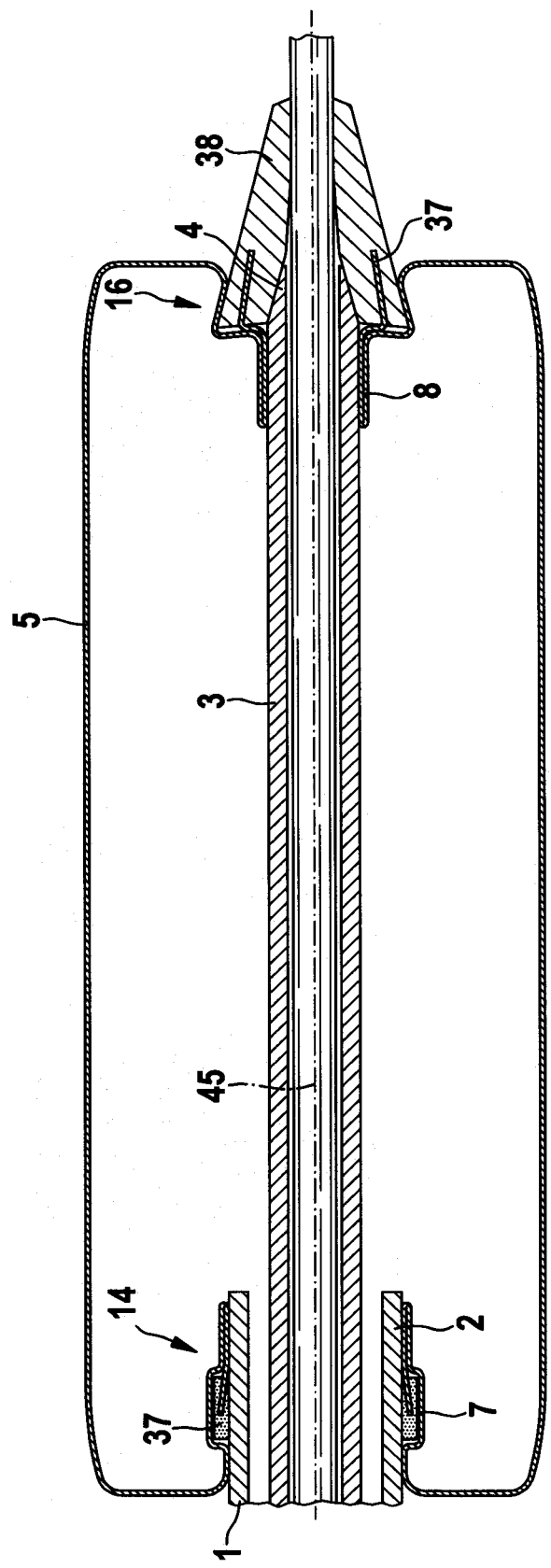
FIG. 18 shows a schematic longitudinal section of the distal end region of a balloon catheter with self-sealing, inverted balloon ends.

In the embodiment shown in FIG. 18, the proximal and distal ends 7, 8 of the balloon 5 are inverted inwardly, and are affixed to the distal end 2 of the outer shaft 1 and to the distal end 4 of the inner shaft 3 via corresponding connections 37. Duration dilation of the balloon, the corresponding weld or glue seams of the connection 37 are subjected only to compression stress as the result of this inwardly rolled attachment of the balloon 5. It is important to ensure that the ends 7, 8 of the balloon 5 in the inverted region are stacked on themselves in two layers. Overall, the configuration shown in FIG. 18 results in an untapered balloon having self-sealing attachment zones 14, 16 at the outer shaft and the inner shaft 3.

Figure 19:
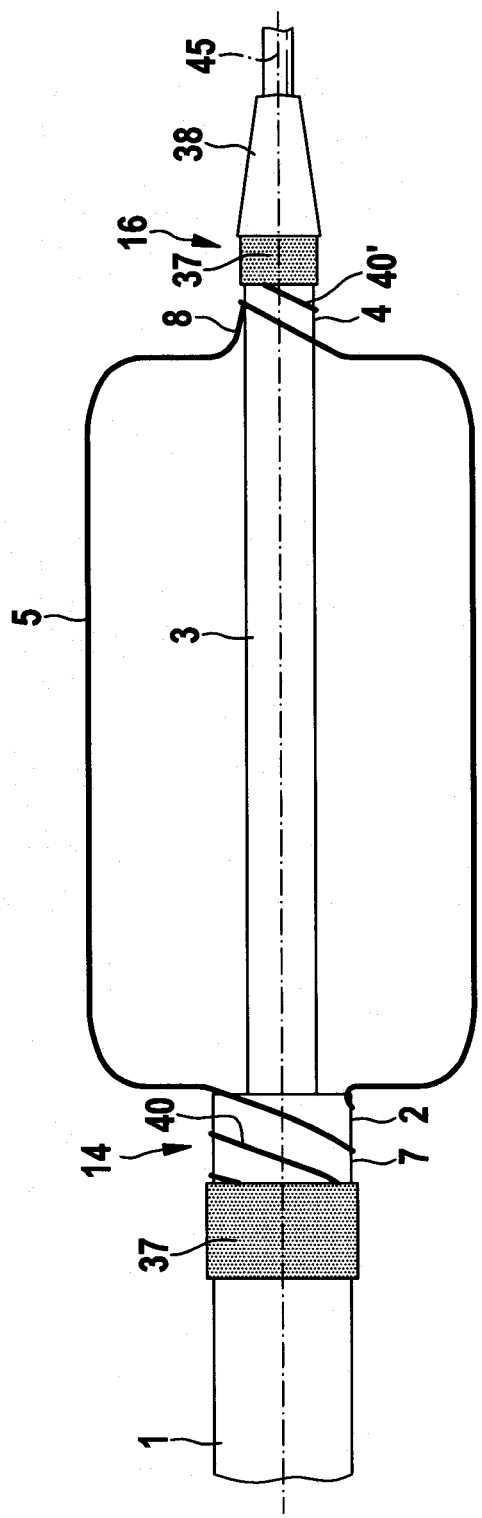
FIG. 19 shows a schematic longitudinal section of the distal end region of a balloon catheter having twisted balloon ends.

FIG. 19 shows a further design of a balloon catheter in which an untapered balloon 5 is constricted at each of its two ends 7, 8 by twists 40, 40', having the same rotational direction, in front of the actual proximal and distal attachment zones 14, 16, respectively. In these two attachment zones 14, 16 a connection 37 in the form of a weld or an adhesive bond of the balloon 5 is once again provided on the outer shaft and inner shaft 1, 3, respectively. Here as well, the connection of the balloon to the respective shaft is thus protected from peeling stress. The inner shaft and outer shaft 1, 3 must be secured to one another in a rotationally fixed manner to prevent the balloon ends 7, 8 from becoming untwisted.

A guide wire 45 for the catheter is shown in the lumen of the inner shaft 3 in all the embodiments according to FIG. 14 through 19.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A balloon catheter, comprising:
   an outer shaft having a distal end and a fluid line;
   an inner shaft, provided at least at the distal end of the outer shaft, which projects beyond the distal end of the outer shaft; and,
   a balloon which is dilatable under the influence of a fluid introduced through the fluid line under pressure, and which
      at its proximal end is attached in a fluid-tight manner to the distal end of the outer shaft at a first attachment zone,
      at its distal end is attached in a fluid-tight manner to the distal end of the inner shaft at a second attachment zone, the balloon being adhered to the inner shaft along an entire length of the second attachment zone, and
      between the attachment zones, in the undilated state is placed in longitudinal folds along its length, characterized in that
   the balloon, at its distal end, has an untapered design with a thin wall thickness which is essentially unchanged over the length of the balloon, and the longitudinal folds extend into the second attachment zone at that location.

2. The balloon catheter according to claim 1, characterized in that at its two ends the balloon has an untapered design with longitudinal folds in the attachment zones.

3. The balloon catheter according to claim 1, characterized in that the balloon is welded at its longitudinal folds in the attachment zones to one or more of the outer shaft and inner shaft in a fluid-tight manner, using a shrinkable sleeve with thermoplastic deformation.

4. The balloon catheter according to claim 3, characterized in that the inner shaft has an extension piece at its distal end which is attached by means of the welded-on balloon.

5. The balloon catheter according to claim 1, characterized in that the inner shaft extends over the entire length of the outer shaft, forming the fluid line in the form of an annular channel.

6. The balloon catheter according to claim 1, characterized in that the outer shaft is designed as a dual-lumen shaft, having a wire lumen which extends over at least a portion of the length of the catheter, and a balloon lumen as a fluid line, the inner shaft being connected to the wire lumen at the distal end of the dual-lumen shaft and extending only from that point to beyond the distal end of the balloon.

7. The balloon catheter according to claim 1, characterized in that the balloon is acted on by at least one constricting ring in front of one or more of the first and second attachment zones of the balloon, the constricting ring having two ends, at least a portion of the balloon passing through the constricting ring and extending beyond both of the constricting ring ends.

8. The balloon catheter according to claim 7, characterized in that the constricting ring is formed by a fiber tow embedded in a fixation matrix, and wherein the at least one constricting ring comprises first and second constricting rings, the first constricting ring surrounding the outer shaft, and the second constricting ring surrounding the inner shaft.

9. The balloon catheter according to claim 8, characterized in that a counterpressure chamber is provided in each of the proximal and distal ends of the balloon, a first counterpressure chamber defined between a portion of the first constricting ring and the outer shaft, a second counterpressure chamber defined between a portion of the second constricting ring and the inner shaft.

10. The balloon catheter according to claim 7, characterized in that one or more of the distal end of the balloon and the constricting ring is provided at a pointed taper located at the distal end of the inner shaft.

11. The balloon catheter according to claim 7, wherein said constricting ring includes a first longitudinal section having a first interior diameter and a second longitudinal section having a second interior diameter that is smaller than the first interior diameter, the first and second sections connected by a stepped shoulder, a portion of the balloon passing over and adjacent to the second interior diameter.

12. The balloon catheter according to claim 11, further comprising a counterpressure chamber at least partially defined by the first longitudinal section and the stepped shoulder of the constricting ring and one of the inner shaft and the outer shaft.

13. The balloon catheter according to claim 7, wherein the balloon is secured with a portion thereof sandwiched between a portion of the constricting ring and one of the inner shaft and the outer shaft.

14. The balloon catheter according to claim 1, characterized in that the balloon, at least in its proximal first attachment zone, is attached in one or more of interiorly and with a flush connection to the outer shaft.

15. The balloon catheter according to claim 1, characterized in that one or more of the proximal and distal end of the balloon is attached to one or more of the outer shaft and inner shaft in an inwardly inverted manner.

16. The balloon catheter according to claim 1, characterized in that the balloon is constricted at its proximal and distal ends by a respective twist having the same rotational direction and located within the attachment zone.

17. A method for manufacturing a balloon catheter according to claim 1, in particular having an untapered balloon at the distal end, comprising the following method steps:
   providing the balloon having tapers at its proximal and distal ends,
   welding the balloon at its proximal end together with its taper to the distal end region of the outer shaft in a fluid-tight manner,
   welding the balloon at its distal end,
   placing the balloon in longitudinal folds around the inner shaft,
   cutting off the taper at the distal end, and welding the distal end of the balloon to the inner shaft in a fluid-tight manner.

18. A method according to claim 17, characterized in that the welding of the ends of the balloon placed in longitudinal folds to one or more of the outer shaft and inner shaft of the catheter is carried out using a shrinkable sleeve which is placed around the longitudinal folds at that location.

19. A method according to claim 18, characterized in that the shrinkable sleeve is removed after the thermoplastic weld connection between the balloon and one or more of the outer shaft and inner shaft cools.

20. A method for manufacturing a balloon catheter according to claim 1, in particular having an untapered balloon at the distal end, comprising the following method steps:
   providing a balloon preform having tapers welded onto the outer shaft and inner shaft of the catheter in a fluid-tight manner,
   placing the length of the balloon in longitudinal folds around the inner shaft,
   removing the distal taper of the balloon together with the distal end region of the inner shaft,
   attaching an extension piece to the distal end of the inner shaft, and
   thermoplastic, fluid-tight welding of the balloon at its distal end to the inner shaft and the extension piece, using a shrinkable sleeve which is placed around the longitudinal folds at that location.

21. A method for manufacturing a balloon catheter according to claim 1, in particular having an untapered balloon at the proximal and distal ends, comprising the following method steps:
   providing a balloon preform having tapers at its proximal and distal ends,
   placing the balloon in longitudinal folds around the distal end of the outer shaft and inner shaft,
   cutting off the tapers at the proximal and distal ends of the balloon preform, and
   welding the proximal and distal ends of the balloon placed in longitudinal folds to the outer shaft and inner shaft of the catheter in a fluid-tight manner.

22. A method according to claim 21, characterized in that the balloon preform having tapers at both ends is manufactured in an overall length corresponding to a multiple of the length of a balloon, and for further processing the untapered balloons are produced from this balloon preform by cutting to length.

23. The balloon catheter according to claim 1, further comprising a constricting ring, wherein the longitudinal folds are at least partially sandwiched between the constricting ring and one of the inner shaft and the outer shaft.

24. The balloon catheter according to claim 1, wherein each of the inner and outer shafts have an outer side, and further comprising:
   a first connection surrounding the outer shaft outer side, the first connection having a slot that receives and secures the balloon proximal end therein in an inwardly inverted orientation; and,
   a second connection surrounding the inner shaft outer side, the second connection having a generally tapered shape oriented away from the balloon, the second connection having a slot that receives and secures the balloon distal end in an inwardly inverted orientation.

25. A balloon catheter, comprising:
   an outer shaft having a distal end and a fluid line;
   an inner shaft extending over the entire length of the outer shaft and projecting beyond the distal end of the outer shaft; and,
   a balloon which is dilatable under the influence of a fluid introduced through the fluid line under pressure, and which:
   at its proximal end is attached in a fluid-tight manner to the distal end of the outer shaft at a first attachment zone using a shrinkable sleeve,
   at its distal end is attached in a fluid-tight manner to the distal end of the inner shaft at a second attachment zone using a shrinkable sleeve, the balloon being adhered to the inner shaft along an entire length of the second attachment zone, and
   between the attachment zones, in the undilated state is placed in longitudinal folds along its length, characterized in that:
   the balloon, at its distal end, having an untapered design with a thin wall thickness which is essentially unchanged over the length of the balloon, and the longitudinal folds extend into the attachment zone at that location;
   the balloon being constricted at its proximal and distal ends by a respective twist having the same rotational direction and located within the attachment zone; and,
   a first constricting ring proximate to the first attachment zone and arranged about the outer shaft with at least a portion of the balloon passing through the first constricting ring, and a second constricting ring proximate to the second attachment zone and arranged about the inner shaft with at least a portion of the balloon passing through the second constricting ring.

* * * * *